United States Patent [19]

Bowen

[11] Patent Number: 4,744,759
[45] Date of Patent: May 17, 1988

[54] INSERTS FOR COMPOSITE DENTAL RESTORATIONS

[75] Inventor: Rafael L. Bowen, Gaithersburg, Md.

[73] Assignee: American Dental Association Health Foundation, Washington, D.C.

[21] Appl. No.: 862,706

[22] Filed: May 13, 1986

[51] Int. Cl.$^4$ .......................... A61C 5/04; A61K 6/02
[52] U.S. Cl. .................... 433/228.1; 106/35; 433/212.1; 433/226
[58] Field of Search ............... 106/35; 433/226, 228.1, 433/202.1, 212.1, 201.1

[56] References Cited

U.S. PATENT DOCUMENTS

| | | | |
|---|---|---|---|
| 3,066,112 | 11/1962 | Bowen | 523/116 |
| 4,215,033 | 7/1980 | Bowen | 106/35 |
| 4,234,310 | 11/1980 | Leuthard | 433/228 |
| 4,376,673 | 3/1983 | Cheung | 433/228.1 |
| 4,380,432 | 4/1983 | Orlowski et al. | 433/219 |
| 4,514,527 | 4/1985 | Bowen | 523/115 |
| 4,521,550 | 6/1985 | Bowen | 523/116 |

OTHER PUBLICATIONS

Lutz et al., "Wear-Resistant MOD Composite Restorations with Ceramic Centric Stops-Results After Four Years," *Quintessence International*, May 1980.

Bowen et al., "Semiporous Reinforcing Fillers for Composite Resins: I. Preparation of Provisional Glass Formulations," J. Dent. Res. 55: 738–747 (1976).

Bowen et al., "Semiporous Reinforcing Fillers for Composite Resins: II. Heat Treatments and Etching Characteristics," J. Dent. Res. 55:748–756 (1976).

Bowen et al., "Theory of Polymer Composites," *International Symposium on Posterior Composite Resin Dental Restorative Materials*, 95–107 (Peter Szulc Publishing, The Netherlands, 1985).

Zidan, "Etched Base-Metal Alloys: Comparison of Relief Patterns, Bond Strengths and Fracture Modes," Dental Materials 1: 209-213 (1985).

*Primary Examiner*—Paul Lieberman
*Assistant Examiner*—Linda D. Skaling
*Attorney, Agent, or Firm*—Allegretti, Newitt, Witcoff & McAndrews, Ltd.

[57] ABSTRACT

Means to decrease the effects of polymerization shrinkage, increase stiffness, decrease the coefficient of thermal expansion and improve the durability of composite restorations by use of inserts are disclosed. Pieces of an aluminoborosilicate glass are phase-separated by heating to 870° C. for 2 hours producing opaque inserts with silica-rich surfaces. Boiling for 1 hour in aqueous 0.5 N NaOH solution removes the surface layer, and produces a rough-textured surface with increased area. The surface texture plus treatment with an organofunctional silane provides for both micromechanical and chemical bonding with composite resins. Cavities in teeth are partially filled with unhardened composite material, and inserts of appropriate size and shape are pressed into the cavity so that the insert constitutes as much as possible of the finished restoration and its surface. The excess extruded composite material is removed with a hand instrument, and the composite containing the insert is light cured. The glass insert, together with the surrounding hardened composite, is contoured with high-speed rotary diamond instruments. Alternative types of inserts are also described.

29 Claims, No Drawings

INSERTS FOR COMPOSITE DENTAL RESTORATIONS

The work described herein was supported, in part, by USPHS Research Grant DE-5129-08 to the American Dental Association Health Fundation from the National Institutes of Health-National Institute for Dental Research.

BACKGROUND OF THE INVENTION

This invention relates to the field of dental restorations, and in particular to the field of composite resin restorations including those in cervical, occlusal or posterior interproximal sites. Composite dental restorative materials are described in U.S. Pat. No. 3,066,112, issued in November 1962. Current practice in filling cavities with cosmetically appealing compostions involves the use of resins mixed relatively homogeneously with a very finely divided or colloidal filler and inserted into the dental cavity. Demand has increased for placement of composite restorations in posterior teeth. There are a number of factors that contraindicate the use of the composite (resin plus filler) compositions for occlusal or posterior interproximal restorations. Some of these include the problem of polymerization shrinkage, which can result in contraction gaps and microleakage of gingival margins of restorations; a low stiffness (modulus of elasticity), which can result in loss of support of remaining tooth structures; and loss of restoration contour where contacted by cusps of the opposing dentition, which can lead to malocclusion. This latter problem is the most serious; the composite resin restorations tend to crack, break down and wear away where the cusps of opposing teeth contact or closely approach the restorations.

Composite resin dental materials of this type are, for example, described in U.S. Pat. No. 4,215,033, issued July 29, 1980, and in Bowen et al., "Semiporous Reinforcing Fillers For Composite Resins: I. Preparation of Provisional Glass Formulations," 55 *J. Dent. Res.* 738–47 (1976), and Bowen et al., "Semiporous Reinforcing Fillers For Composite Resins: II. Heat Treatments and Etching Characteristics," 55 *J. Dent. Res.* 748–56 (1976). See also, Bowen et al., "Theory of Polymer Composites," *International Symposium on Posterior Composite Resin Dental Restorative Materials,* 95–107 (Peter Szulc Pub., The Netherlands, 1985), and references cited in each of the above articles and patent.

U.S. Pat. No. 4,215,033 in particular describes a transparent glass filler material in which the glass is separated into two interconnected vitreous phases which after crushing and ball milling to a very fine powder, is acid etched to produce a porous surface layer. Preferred glass compositions disclosed in this patent include a mixture of silicon dioxide, boron oxide, aluminum oxide and strontium oxide, with one or more from the group of calcium oxide, zinc oxide, stannic oxide, and zirconium oxide as optional modifying ingredients. The transparent inorganic glass particles of microscopic size are silane treated and then combined with an organic resin to provide an improved composite dental material.

SUMMARY OF THE INVENTION

The present invention provides estheti or metallic inserts for direct-filling dental restorations in the form of relatively large individual pieces sized and shaped to fill a cavity as nearly as possible with a single piece or perhaps two pieces, and designed to be cemented into place with a composite resin.

It is an object of this invention to reduce the hardening shrinkage previously associated with the use of composite materials in restorations. It is a further object of the invention to increase the stiffness (modulus of elasticity) of composite fillings. It is an additional object of the invention to maintain X-ray opacity (comparable to dentin and enamel) in composite fillings (important in back teeth in particular), while providing the visual opacity necessary for esthetic appearance of the restoration. Another object of the invention is to improve (lower) the coefficient of thermal expansion of the restoration to more nearly match the tooth crown.

The most important object of the instant invention is to improve the wear characteristics of composite restorations by providing a solid surface (as opposed to a composite material) to come into contact with or closely approach the opposing teeth and/or the proximal tooth.

In general, the invention relates to a rapid method of making surface-roughened solid pieces for use as inserts in composite restorations. The inserts are not designed to fit the cavity preparations exactly as do precision casting custom-made in dentistry; custom-made precision castings are very expensive relative to "direct-filling materials". Direct-filling materials are those with which a dentist can completely restore a dental cavity in a single appointment and procedure. The present invention provides a means to make mass-produced inserts which serve many of the beneficial functions of cast metal inlays or custom-formed porcelain inlays, but with less expense in their fabrication and utilization. The present method allows the preparation and selection of inserts which approximately fill a given dental cavity preparation by selection from a group or set of inserts. The dentist can select an insert which will fit the cavity preparation partly, the rest of the cavity being filled with the composite restorative material.

These inserts can be of metal compositions for use in those areas of the mouth where esthetics is not a consideration, or of glass, microcrystalline glass, ceramic, or porcelain materials where esthetics in the final restoration is important because the tooth is occasionally visible. The most preferred embodiment of the present invention utilized special aluminoborosilicate glass compositions with properties especially suited for the present dental application. These contain silicon oxide, boron oxide, aluminum oxide, strontium oxide, and/or other modifier oxides optionally. These may contain, for example, ranges such as: silica, 33 to 80 mol %; boric oxide, 7 to 33 mol %; aluminum oxide, 1 to 17 mol %; and zinc oxide, 5 to 25 mol %; or strontium oxide, 3 to 33 mol %; or a combination of calcuim oxide plus strontium oxide, about 3 to 33 mol %; or calcium oxide plus strontium oxide plus zinc oxide, about 3 to 33 mol %; and other modifiers and oxides may also be incorporated including magnesium oxide, zirconium oxide, tin oxide, titanium oxide, niobium oxide, tantalum oxide and tungsten oxide. One of the most preferred compositions in mol % is silicon dioxide, 58; boric oxide, 16; aluminum oxide, 5; and strontium oxide, 21 mol %. Another contains 60, 16, 5, and 20 mol % of the same oxides, respectively.

In the most preferred embodiment, the mix is melted to form a liquid. The liquid is mixed to homogenize it, and the molten glass liquid is then poured in between water-cooled rollers which are synchronized and shaped such as to form objects of assorted sizes and shapes appropriate for partially filling typical dental cavities. These shaped pieces are then heat-treated to obtain visually opaque objects (as opposed to the transparent frit particles of the prior art U.S. Pat. No. 4,215,033) with an internal phase separation into two phases that match the appearance of composite restorations and the crowns of natural teeth. The heat-treated pieces can be trimmed (if necessary), selected, and sorted for size and type and then, in batches, etched, preferably by heating in strong aqueous base solution (for example, 0.5N sodium hydroxide solution), to remove a silica-rich surface skin which develops during the heat-treatment process, and provide a rough-textured surface with increased area for improved bonding with the dental composite resin. The rough surfaces of the pieces are then treated with an organofunctional silane coupling agent and packaged for sale to dentists in compartments segregated according to suitable sizes and shapes from which the dentist can select an insert for a given dental cavity preparation.

The resulting pieces for inserts are, as a further aspect of the invention, employed in a method for repairing cavities in teeth comprising partially filling the cavities with unhardened composite material, pressing an insert piece prepared as described above into the composite material, removing excess extruded composite material, curing (hardening) the composite material, and contouring the surface of the insert and hardened composite material to the appropriate contour which includes optimal contact with adjacent or opposing teeth. The invention further contemplates a repaired tooth assembly prepared by the methods described above.

Alternative embodiments of the invention involve the use of etchable metal inserts in locations where esthetics is not important, or other glass or microcrystalline glass compositions, and other etchable inserts such as pieces of ceramic, microcrystalline glass or porcelain formulated to match the appearance of tooth surfaces and prefabricated by mass-production methods to allow for direct-filling restorative procedures.

DESCRIPTION OF THE PREFERRED EMBODIMENTS

The scope of phase separable aluminoborosilicate glass compositions preferred for inserts of the present invention overlaps in reactant compositions and initial processing steps with certain of the glasses described in U.S. Pat. No. 4,215,033. These include compositions of about 33 to about 80 mole percent silicon dioxide, about 7 to about 33 mole percent boron oxide, about 1 to about 17 mole percent aluminum oxide and about 5 to 25 mole percent zinc oxide, or about 3 to 33 mole percent strontium oxide, or 3 to 33 mole percent calcium plus strontium oxides, or about 3 to 33 mole percent calcium oxide plus strontium oxide plus zinc oxide.

The complete disclosure of U.S. Pat. No. 4,215,033, issued July 29, 1980, is expressly incorporated herein by reference.

The disclosure of that patent describes a preferred heat treatment at 720° C. for 20 hours to yield a transparent phase-separated glass frit for use in preparing reinforcing fillers for composite resins. After pulverizing in a ball mill, the frit described in the aforesaid patent provided a powder with surfaces that could be etched with acids; transparency and refractive indices approximated those of the polymerized resin. The transparency of that glass frit is unsatisfactory for use in the present invention, in which the appearance of the glass must approximate that of the tooth surface, not the resin.

In conjunction with the present invention, it has been found that a phase serparable glass such as Glass no. 5 (K423) can be made to develop the desired degree of visual opacity comparable to that of the tooth crown upon heat treatment at about 870° C. for 2 h. The insert would then harmonize with the restoration and the appearance of the tooth dentin and enamel, whereas the prior art glass frit approximated in transparency and refractive index the parameters of the polymerized resin. Specimens of this glass, containing 58 mole % $SiO_2$, 16 mole % $B_2O_3$, 5 mole % $Al_2O_3$ and 21 mole % SrO heated for 2 hours at 870° C., developed an opaque appearance, for tooth-matching esthetics, without excessive slumping or loss or original contour.

In order to anchor the insert in the composite resin, it is desirable that there be a micromechanical bonding mechanism, as well as the silane chemical bonding mechanism between the composite resin and the glass insert surface. In order to accomplish this micromechanical bonding mechanism, the insert surface is etched, that is, rendered rough or slightly porous. Existence of the microporosity may be tested for by following the absorption of methylene blue stain. In the glass frit compositions of U.S. Pat. No. 4,215,033, microporosity was achieved by etching the two-phase glass surfaces with acid, preferably phosphoric acid. The crushed frit particles of the moderately heat-treated glass frit of U.S. Pat. No. 4,215,033 responded to a solution of three normal phosphoric acid containing 0.05% methylene blue after immersion for 3–5 minutes as evidenced by visible blue stain. In contrast, the preferred heat-treated glass inserts of the present invention do not respond to the application of an acid solution of three normal phosphoric acid containing 0.05% methylene blue, even after more than 30 minutes. As an aspect of the present invention, it has been discovered that not acid, but alkali treatment of the inserts will cause them to respond to methylene blue solution, as evidenced by an even, light blue stain after immersion for 7 minutes. The preferred alkali treatment is boiling in sodium hydroxide solution, most preferably 0.5N NaOH. Inserts treated with the boiling sodium hydroxide solution and immersed in a 0.1% aqueous methylene blue solution containing acid also developed an even, light blue stain. It is hypothesized that the boiling sodium hydroxide solution not only dissolved the thin high-silica surface layer, but also produced a roughened surface with greater surface area by differential dissolution of the two phases separated by the heat treatment. It is further hypothesized that although the silica is soluble in boiling sodium hydroxide solution, one the surface skin of silica is removed, the low-silica-phase components dissolve even more rapidly than does the high-silica phase. This then yields a high-silica surface having a high surface area upon which the methylene blue indicator can be absorbed as a test of increased surface area and roughness.

Optionally, one or more solutions can be used at ordinary or elevated temperatures to produce the desired increased surface area and roughening of the insert surface. For glass, vitreous multiphase glass, microcrystalline glass, ceramic, and porcelain compositions which tend to form silica-rich surface layers during their fabrication and/or heat treatment, surface roughening by means of an aqueous base solution, preferably at elevated temperature, is preferred. For this, bases such as NaOH, KOH, sodium or potassium carbonate or bicarbonate can be used. Subsequently, after the silica-rich surface has been removed and the underlying substrate altered by the action of the base, the insert may be further treated with acids such as phosphoric, nitric, sulfuric, oxalic, pyruvic, or mixtures of these or other acids to further roughen or alter the surface.

Alternatively, silica-rich surfaces on inserts can be treated with fluoride-containing compounds such as NaF, KF, $NH_4HF_2$, or $NH_4F$ separately or combined with bases.

In the case of metal inserts comprised of pure metals or alloys, mass-production forming methods are essentially the same as described for silicious inserts. That is, the molten metal or alloy is cast into the desired insert shapes and sizes by quenching in water, air, or other cooling medium, or preferably by the melt being poured between synchronized water-cooled rollers having complementary surface shapes that will mold and form the pieces as the melt is being solidified. Because precision castings are not required, these or other known methods for rapid multiple or semi-continuous casting or forming methods can be used. Arrays of molds can be formed (with reusable patterns) having multiple insert forms connected with short sprues in series. After casting and acid etching, these arrays can be cut apart (with high-speed separating discs used in dental laborator technology) or broken apart to give objects of sizes and shapes useful as inserts for dental composite restorations. The investments for such multiple casting can be of a coarse-textured sand-like nature which provides surface roughness to the objects. Otherwise, it can consist of two plates of a durable material shaped to form the multiple insert castings, designed to separate following themolding and thereby be reusable.

Metals and alloys suitable for use as inserts for composite dental restorations include titanium and titanium alloyed with one or more metals including Al, Cu, Mn, V, Sn, Fe, and Cr; also, "base-metal alloys" used in dentistry such as those containing Ni, Cr, Mo, and Be; or Ni, Cr, V and Be; or Ni, Cr, and Mo; or Co, Cr, and Mo (see Zidan, O.: *Dental Materials* 1985: 1: 209-213); and also, other metals and alloys including noble metal alloys used in dentistry.

The surface etching of metal and alloy inserts can be accomplished by subjecting the objects to acid solutions containing nitric, hydrochloric, sulfuric, oxalic, citric, phosphoric, or combinations of these at normal or elevated temperatures for a time of two minutes to two days, depending on the metal and the acid solution used. When sufficiently etched, the surface of the object has a dull, non-reflective appearance and appears rough when viewed with magnifications. The rough metal surface is cleaned and dried and then treated with the silane (3-methacryloxypropyltrismethoxy silane) or one or more of the adhesion-promoting formulations described in U.S. Pat. Nos. 4,514,527; issued Apr. 30, 1985; 4,521,550 issued June 4, 1985; pending application Ser. No. 699,079 filed Feb. 7, 1985; or pending application Ser. No. 825,319 filed Feb. 3, 1986.

Ceramic, porcelain, and microcrystalline glass compositions are used in various other aspects of dentistry. They are custom-fabricated for precision-filled crown or bridge facings, inlays or crowns. Porcelain teeth are used for dentures. Compositions and methods of fabrication are well known in the dental laboratory arts. One embodiment of the present invention is the mass production of inserts for composite dental restorations utilizing these materials. This can be accomplished by forming sequential "strings" of contiguous objects of the appropriate shape and size for inserts and then breaking apart the individual segments before or after treatment with a strong aqueous alkali solution, preferably heated, followed by treatment with a strong acid solution, a solution containing a fluoride compound, and/or a concentrated phosphoric acid solution, preferably heated. After washings and drying, these separated objects for use as inserts are then treated with 3-methacryloxypropyltrismethoxy silane. The range of sizes and shapes and "shades" (a dental term for colors as well as lightness and darkness, used to match appearance of teeth and/or composite materials) are then segregated into compartments and sold to dentist in "kits" (containers having instructions for use, and ancillary materials and equipment).

Clear, homogeneous glass compositions prepared as described hereinabove for use as inserts are also within the scope of the present invention. The advantages and disadvantages of clear glass inserts are: the dentist would get more thorough hardening of the light-cured composite formulation because of better light transmission through a clear insert to the underlying composite mateial, might be able to inspect the underlying material by visible means subsequently, and could readily distinquish what part of the restoration was insert and what part composite; however, disadvantages would include an appearance of the restoration lacking natural esthetics, and difficulty of getting surface roughness for micromechanical bonding between the insert and the composite resin by treatment with alkali, fluoride, and/or acid etching.

Adhesion of the insert to the composite resin is enhanced by silane treatement of the surface of theinsert prior to its placement in the composite resin situated in the cavity. In general, a homogeneous solution of organofunctional silan is prepared, inserts are added to the solution, the mixture is stirred gently to avoid abraision of the insert surfaces for a period of time, such as 30 to 60 minutes, excess solution is removed and the beads are dried and then heated to about 100° to 150° C., preferably about 120° C. in an evacuated and/or vacuum oven to condense the silane on the roughened insert surface. A preferred silane composition for use in this step of the invention is 3-methacryloxypropyltrismethoxysilane.

Inserts should be selected to fit the size and shape of the cavity as nearly as possible. Optionally, the surface of the cavity may be prepared by treatment according to the methods of U.S. Pat. Nos. 4,514,527 and 4,521,550 and pending application Ser. No. 699,079 filed Feb. 7, 1985 and pending application Ser. No. 825,319 filed Feb. 3, 1986 herein after referred to as "adhesion-promoting formulations and techniques". The cavity is then partially filled with soft composite resin (the cavity walls and matric, if any, being covered) and the insert selected for the area is forced into the unset composite and can optionally be held under pressure during curing. Preferably, a light-curing type of composite resin is used which can be quickly hardened by the application of a curing light. Excess unset resin is removed from around the insert before the composite is hardened. The cured composite and insert are then contoured by the use of high-speed rotary diamond instruments with water cooling and high-volume evacuations.

Alternative embodiments include the use of different glass compositions for the inserts, or use of inserts of microcrystalline glass, ceramic, or porcelain materials. Etchable metals, in restorations where esthetics are not important, can also be used.

As an additional alternative embodiment, further resin devoid of or containing reinforcing fillers (the resin being preferably of the light-cure type) may be applied on top of the contoured insert and composite restoration, and extended over surrounding enamel, subsequent to acid etching, washing, and drying of these three surfaces.

The nature of the present invention may be better understood by consideration of a comparison between the invention and the teachings of U.S. Pat. No. 4,215,033. The differences are many.

With respect to the patented material, the frit particles are preferably ground to the smallest particle size feasible (but see col. 14, lines 58–62), whereas in the instant invention, the particles are as large as possible to fit into dental cavity preparations. The fractured surfaces exposed in the frit disclosed in the patent can be etched with acids; however, in the instant invention the heat-treatment of the particle surface for particles of preferred composition alters the nature of the surface so that it cannot be etched with acid but requires etching with boiling sodium hydroxide solution or the equivalent to remove the high-silica surface and produce a roughened insert surface.

The frit of the cited patent reuires phase-separation with the phases having dimensions smaller than the wave-length of visible light so that the particles will be transparent, whereas in the present invention the phase-separation differs in that it provides phase dimensions comparable and approximately the same as the wave-length of visible light so as to give a white, visually opaque appearance in order to match tooth crowns and composite restoration materials. For the frit of the paten to obtain such fine phase dimensions, glass compositions were necessarily close to the immiscibility demarcation of the glass fromulations whereas for the present invention compositions farther into the two-liquids region are employed to obtain the coarser structure necessary. The refractive index of each prior art frit particle had to match the resin of the composite almost exactly to prevent an unnatural appearance to the composite restoration, whereas in the present invention the refractive index need not be a close match of the composite resin and, therefore, higher silica content formulations are used to improve the chemical durability of the insert which will constitute a large portion of the final dental restoration.

With respect to the frit of the patent, the X-ray opacity of the reinforcing filler particles had to be higher because the frit particles are intermixed with approximately equal parts of an X-ray transparent organic polymeric resin, whereas in the present invention the optimum X-ray opacity of the solid insert which will not be diluted by resin internally is lower so as to match the X-ray opacity of the composite resin which surrounds it in the tooth and it comparable so that both will be comparable to the X-ray opacity of human dentin and enamel.

There are significant differences, also, which are pertinent to quality control during manufacture. In production of the frit of the patent, there was no apparent way for the manufacturer to know if the transparent glass was phase-separated or not, so that sophisticated BET surface-area measurements or etching and staining reactions with cationic dyes such as methylene blue were required, whereas with composition of the present invention the heat treatment renders the object visually opaque which simplifies the quality control in the production of the inserts of the present inventon. In the frit of the patent the surface asperities for micromechanical bonding between the resin and the filler particles had to be very small in size because of the very small size of the average filler particle itself, whereas in the present invention the large insert can have surface roughness with surface irregularities and asperities very much larger because of the larger size of the insert itself. Furthermore, with the patented frit the very fine surface texture was beyond the power of resolution of scanning electron microscopes and visual microscopes, whereas in the present invention the surface roughness characteristics can be large enough for easy visualization with visual, ultra-violet, or scanning electron microscopy so as to ascertain the surface characteristics of the products.

The patented frit did not provide a dental restoration with a coefficient of thermal expansion as low as the natural crown, because the composite itself cannot contain sufficient filler material, and consequently its coefficient of thermal expansion is approximately three times higher than that of the tooth crown; whereas the present invention allows utilization of glass, ceramic, porcelain, or metal inserts the coefficients of thermal expansion of which are nearly the same as that of tooth crowns. Therefore, the ultimate restoration which contains the insert as a major volumetric component has a coefficient of thermal expansion much closer to that of the natural tooth crown.

In the patented frit the shapes of the particles for a feasible commerical composite are random and irregular due to the nature of their formation by ballmilling to get sufficiently small sizes, whereas the present invention teaches methods of forming specific particles shapes by mass production methods such that by selection the dentist can fill the bulk of a given cavity with an individual piece of insert material.

In addition, the patented frit cannot provide a dental restoration with a hardness, stiffness (modulus of elesticity), or dimensional stability to the extent that the present invention can provide. The former teaches a filling material which has detrimental polymerization shrinkage, whereas the present invention provides an insert which does not shrink and reduces the shrinkage upon hardening of the overall restoration. Also, the former results in a restoration surface that is relatively rough in texture due to the differences in properties between the reinforcing filler and the resin for high-filled ("macro-filled") composites; for "micro-filled" composites, which have reinforcement particles smaller than colloidal (mainly in the submirometer size range), relatively small amounts of reinforcing filler can be incorporated with subsequent decrements of desirable physcial properties such as stiffness, and other properties; whereas the present invention allows the surface of the restoration corresponding to the insert to be smooth and highly polishable.

The invention is illustrated by the following examples.

EXAMPLE 1

Composition and Heat Treatment

Glass objects were prepared through the water quenching step in accordance with the teachings of U.S. Pat. No. 4,215,033. The reactant composition for the glass (no. 5; K-423) was approximately 58 mole percent silicon dioxide, 16 mole percent boron oxide, 5 mole percent aluminum oxide and 21 mole percent strontium oxide. Pieces within the size range of 2–4 mm were selected. The pieces of glass consisted of roundish particles of irregular shapes and sizes resulting from the molten glass having been poured into water. (For the present feasibility study the particles were simply selected according to sizes. For commercial dental applications, they could be formed itno appropriate shapes and sizes roughly approximating what the normal filling would be by the use of water-cooled rollers having the desired surface shapes.) The samples for use as inserts were then heat treated for 2 hours in a gradient furnace. Specimens heated for two hours at 870° C. developed a visual opacity substantially within the range of human dentin and enamel without excessive slumping or less of original contour. For tooth-matching esthetics, however, a temperature higher than 840° C. or lower than 900° C. for two hours could be used, or lower temperatures for periods longer than 2 hours. The higher temperatures gave inserts of more rounded shapes.

EXAMPLE 2

Visual Opacity

Flat, heat-treated objects of composition no. 16 (K-540 U.S. Pat. No. 4,215,033) about 1 mm thick, formed by quenching between water-cooled rollers with smooth surfaces, were placed alongside 1 mm thick sections of dentin and enamel from extracted human teeth, under water on a black and white striped cardboard after heating 2 or 3 hours at 850° C. These were compared to opacity standards prepared for ADA Specification No. 9. The image of the stripe was clearly visible through the heat-treated glass sample. However, a quantitative comparison of the contrast ratio ($C_{0.70}$) with the tooth section or opal glass standards (the minimum (0.35) and maximum (0.55) range recommended by the ADA Specification; the average opacity for enamel if 0.39 and for dentin is 0.70) was confounded by the finer texture and preferential scattering of blue light by the heat-treated glass sample. When inserts of this composition and heat treatment were placed in composite resin restorations in extracted teeth, the opalescent to semi-opaque appearance gave an unnatural bluish tinge from back-scattered light. More sever heat treatments gave excessive slumping or remelting.

EXAMPLE 3

Microcrystalline Glass Inserts

Inserts were prepared from a zinc glass (No. 15; K-437; U.S. Pat. No. 4,215,033) containing 53.6 mol % $SiO_2$, 11.6 $B_2O_3$, 11.6 $Al_2O_3$, and 23.2 ZnO. Upon heat treatment, visual opacity developed at temperatures above 850° C. (2 h) with the formation of a microcrystalline glass. The inserts did not sag or slump below 900° C. (2 h).

EXAMPLE 4

Alkali Treatment

Heat-treated samples prepared in accordance with Example 2 were immersed in a 0.5N NaOH aqueous solution in a covered 5 ml beaker, placed on a hot plate, and heated gradually to achieve boiling for a total of one hour.

EXAMPLE 5

Alkali and Acid Treatments

Samples prepared according to Example 1 were immersed in a strong aqueous base solution and then after rinsing with water were additionally treated with a solution of phosphoric acid at room temperture. These gave a positive methylene blue test for a roughened, increased surface area as did those in Example 4. Those treated with only the acid did not pass this test.

EXAMPLE 6

Silane Treatment

A silane solution was prepared by adding 0.98 g of water to 0.2 g of silane A-174 (3-methacryloxypropyltrismethoxysilane, Union Carbide, New York, NY) and adjusting the pH of the solution to about 4.0 by adding small drops of concentrated acetic acid, and agitating the mixture until it became homogeneous. To this solution were added about 20 glass inserts prepared in accordance with examples 2 and 3, and the mixture was magnetically stirred for about 30 minutes. Excess solution was filtered through a medium-pore fritted disc. The inserts were dried in air and then heated to 100° C. for 30 minutes in a vacuum oven.

EXAMPLE 7

Restorative Techniques

Extracted teeth were arranged and mounted in dental stone to simulate a lower right quadrant of posterior teeth. A mesio-occlusal cavity was prepared in the lower right first molar while the distal surface of the second bicuspid was protected from damage with a metal matric and a wooden wedge.

Inserts prepared according to Examples 2, 4, and 6 were selected to fit the size and shape of the interproximal box and occlusal surface of the preparation. The interproximal insert was selected so it would have a maximum area of contact with the distal surface of the second bicuspid. The particle selected for the occlusal central fossa was also selected to fill the prepared cavity as well as possible.

The dentin surfaces were covered with $Ca(OH)_2$ (Life, Kerr Dental Products Company, Sybron, Inc., Rommulus, Mich.). The beveled enamel surfaces were ethed with a 37% phosphoric acid etchant gel (Bisco). A light activated bonding resin (Bisco, lot #112884) was applied to all of the cavity surfaces. A clear matrix (Premier Dental Products, Norristown, Pa.) and a clear plastic wedge were applied. A light-cured composite (BIL-FIL-I TM Posterior Restorative Composite, light shade (59), lot #083184) was condensed into the interproximal box. The insert selected for that area was then forced into the unset composite and held under pressure. Pressure was maintained while the composite was cured with a curing light (Prisma-Lite TM, the L. D. Caulk Co., Milfored, Del.). The light was applied from the buccal and lingual surfaces through the clear matrix and wedge. The occlusal area of the interproximal was then slightly overfilled, and the central fossa was filled by forcing an insert into unset composite in that part of the cavity. Excess composite was removed with a hand instrument, an then the unset composite was hardened with the light. Diamond rotary instruments were used to develop the correct occlusal surface contour and to refine the interproximal portion of the restoration. White stones and finishing and polishing disks (Sof-Lex TM, 3M Co., St. Paul, Minn.) were used to obtain the final polish. These in vitro studies demonstrated the feasibility of using inserts for composite dental restorations.

Radiographs were taken before the tooth preparation and after the final finish and polish of the restoration. The X-ray opacity was within an acceptable range.

In a different experiment, matching, nonretention-form class V cavities were prepared in opposite sides of extracted teeth, and the cavities were treated with a dentin and enamel bonding agent (U.S. Pat. No. 4,521,550). Composite restorations were placed in each, one with an insert and the other without. After thermocycling for one week, the resorations with the inserts had less microleakage than did the ones without inserts. The inserts apparently improved bonding and reduced microleakage presumably due to a reduction of hardening shrinkage and a reduction of the coefficient of thermal expansion of the restoration to more closely match that of the tooth crown.

It should be understood that the foregoing disclosure emphasizes certain specific embodiment of the invention and that all modifications or alternatives equivalent thereto are within the spirit or scope of the invention as set forth in the appened claims.

What is claimed is:

1. A method of making an object suitable for use as an insert in a composite dental restoration comprising
   (a) preparing a mix consisting of silicon dioxide and at least one other oxide selected from the group consisting of aluminum oxide, boron oxide, strontium oxide, calcium oxide, zinc oxide, tin oxide, titanium oxide, niobium oxide, magnesium oxide, zirconium oxide, tantalum oxide and tungsten oxide, so as to provide for an x-ray opacity and visual opacity substantially within the range of human dentin an enamel upon treatment as specified hereinafter;
   (b) heating the mix to form a liquid or slurry;
   (c) mixing the liquid or slurry to homogenize it;
   (d) quenching the liquid or slurry to form cooled objects in assorted sizes and shapes, each of said objects being sized and shaped to fill a typical dental cavity as nearly as possible with a single object;
   (e) heat treating the quenched objects to obtain objects having a visual opacity substantially within the range of human dentin and enamel, and separate internal phases;
   (f) etching the objects by treating them with one or more solutions comprising a base or NaF, KF, $NH_4HF_2$ or $NH_4F$ to remove the surface layer and provide an object of rough-textured surface with increased area; and
   (g) applying an adhesion-promoting compound to the objects to form an insert.

2. A method as in claim 1 wherein the mix of subpart (a) comprises about 33 to about 80 mole percent silica, about 7 to about 33 mole percent boric oxide, about 1 to about 17 mole percent aluminum oxide and either (1) about 5 to about 25 mole percent zinc oxide, or (2) about 3 to about 33 mole percent strontium oxide, or (3) about 3 to about 33 mole percent of a combination of calcium oxide plus strontium oxide, or (4) about 3 to about 33 mole percent of a combination of calcium oxide plus strontium oxide plus zinc oxide.

3. A method as in claim 2 wherein the mix of subpart (a) comprises about 58 mole percent silicon dioxide, about 16 mole percent boric oxide, about 5 mole percent aluminum oxide and about 21 mole percent strontium oxide.

4. A method as in claim 2 wherein the mix of subpart (a) comprises about 60 mole percent silicon dioxide, about 16 mole percent boric oxide, about 5 mole percent aluminum oxide and about 20 mole percent strontium oxide.

5. A method as in claim 1 wherein the mix is melted to form a liquid in step (b).

6. A method as in claim 1 wherein the mix is quenched in step (d) by pouring it between cooled rollers synchronized and shaped to form objects of assorted sizes and shapes, each of said objects being sized and shaped to fill a typical dental cavity as nearly as possible with a single object.

7. A method as in claim 1 wherein the objects are heat treated in step (e) to a temperature of at least 850° C.

8. A method as in claim 1 wherein the objects are etched in step (f) by treatment with a strong aqueous base solution.

9. A method as in claim 8 wherein the objects are etched in step (f) by treatment with boiling aqueous sodium hydroxide.

10. A method as in claim 1 wherein the etching was base, NaF, KF $NH_4HF_2$ or $NH_4F$ is followed by treatment with acid.

11. A method as in claim 1 wherein the adhesion-promoting compound of step (g) is an organofunctional silane coupling agent.

12. A method as in claim 11 wherein the organofuncitonal silane coupling agent is 3-methacryloxypropyltrismethoxy silane.

13. A method for repairing cavities in teeth comprising partially filling the cavities with unhardened composite material, pressing an insert, said insert being sized and shaped to fill a typical dental cavity as nearly as possible with a single insert. prepared by the method of claim 1 into the composite material, removing excess extruded composite material, curing the composite material and contouring the surface of the insert and hardened composite material.

14. A method as in claim 13 wherein the cavity surface is prepared befor the introduction of the composite resin by use of adhesion-promoting formulations and techniques.

15. A method as in claim 13 wherein the insert is held under pressure in the composite material while the composite material is cured.

16. A method as in claim 13 wherein the composite material is of the light-curing type and is cured by the application of a curing light.

17. A method as in claim 13 wherein the dentin surfaces are covered with calcium hydroxide and the beveled enamel surfaces are etched with a phosphoric acid etchant gel before the unhardened composite material is placed in the cavity.

18. A method as in claim 13 wherein a bonding resin is applied to the cavity surfaces before the unhardened composite material is placed in the cavity.

19. A method as in claim 13 wherein the surface of the insert and hardened composite material are contoured using a high speed rotary diamond instrument.

20. A method as in claim 13 wherein the surface of the insert and hardened composite material are polished following contouring.

21. A method as in claim 13 wherein additional unhardened composite material is applied and cured following insertion of the insert.

22. The dental restoration comprising the product of the method of claim 13.

23. A method for repairing cavities in teeth comprising protecting the teeth adjacent to the tooth containing the cavity from damage by covering them while the cavity is repaired, covering the dentin surfaces with calcium hydroxide and etching the beveled enamel surface with a phosphoric acid etchant gel, applying a bonding resin to the cavity surface, partially filling the cavity with light-curable unhardened composite material, pressing an insert prepared by the method of claim 1 and selected to approximately fill the cavity into the composite material, removing excess extruded composite material, curing the composite material by the application of a curing light, contouring the surface of the insert and hardened composite material using a high speed rotary diamond instrument, and polishing the surface of the insert and hardened composite material following contouring.

24. The dental restoration comprising the product of the method of claim 23.

25. A kit for the repair of cavities in teeth comprising a selection of inserts of various sizes prepared by the method of claim 1.

26. A method as in claim 1 wherein said mix or the product resulting therefrom is in the form of a molten or slurried form of a glass, vitreous multiphase glass or microcrystalline glass.

27. A method for repairing cavities in teeth comprising partially filling the cavities with unhardened composite material, pressing an insert prepared by the method of claim 26 into the composite material, removing excess extruded composite material, curing the composite material and contouing the surface of the insert and hardened composite material.

28. The dental restoration comprising the product of the method of claim 27.

29. A kit for the repair of cavities in teeth comprising (a) a selection of inserts of various sizes prepared by the method of claim 26, and (b) unhardened composite material suitable for anchoring an insert in a tooth cavity.

* * * * *